United States Patent
Steinert et al.

(10) Patent No.: US 6,952,947 B2
(45) Date of Patent: Oct. 11, 2005

(54) MEASURING HEAD FOR A DEVICE FOR MEASURING THE CONCENTRATION OF A PARAMAGNETIC GAS

(75) Inventors: Günter Steinert, Bad Oldesloe (DE); Alfred Kelm, Badendorf (DE); Hans-Ulrich Hansmann, Barnitz (DE); Hartmut Stark, Stockelsdorf (DE); Peter Dreyer, Pansdorf (DE)

(73) Assignee: Dräger Medical AG & Co., KGaA, Lübeck (DE)

( * ) Notice: Subject to any disclaimer, the term of this patent is extended or adjusted under 35 U.S.C. 154(b) by 32 days.

(21) Appl. No.: 10/612,626

(22) Filed: Jul. 2, 2003

(65) Prior Publication Data
US 2004/0045340 A1  Mar. 11, 2004

(30) Foreign Application Priority Data
Sep. 6, 2002  (DE) ................................ 102 41 244

(51) Int. Cl.$^7$ ............................................ G01N 27/74
(52) U.S. Cl. .................. 73/25.02; 73/25.02; 73/25.01; 73/23.2; 324/204
(58) Field of Search .............................. 73/25.02, 23.2, 73/25.01; 324/204

(56) References Cited

U.S. PATENT DOCUMENTS

| | | | | |
|---|---|---|---|---|
| 2,693,103 A | * | 11/1954 | Krupp ........................ | 73/25.02 |
| 3,292,421 A | * | 12/1966 | Meyer ........................ | 73/25.02 |
| 3,616,679 A | * | 11/1971 | Meyer et al. ............... | 73/25.02 |
| 5,012,669 A | * | 5/1991 | Meyer ........................ | 73/25.02 |
| 5,493,215 A | * | 2/1996 | Otten .......................... | 324/204 |
| 6,430,987 B1 | * | 8/2002 | Stark .......................... | 73/25.02 |

FOREIGN PATENT DOCUMENTS

| | | |
|---|---|---|
| DE | 20 58 633 | 6/1971 |
| DE | 34 00 140 C1 | 10/1984 |
| DE | 100 37 380 | 5/2001 |
| EP | 0 343 519 | 11/1989 |

* cited by examiner

Primary Examiner—Hezron Williams
Assistant Examiner—André K. Jackson
(74) Attorney, Agent, or Firm—McGlew and Tuttle, P.C.

(57) ABSTRACT

A measuring head for the determination of the concentration of a paramagnetic gas in a gas sample has first and second housing parts (21, 2) made of a steel alloy for accommodating a magnet coil body (4, 5) each. The magnet coil bodies extend concentrically around the central axis of each housing part (21, 2). Metallic bars (31, 3), which are used as magnet poles for the measuring head, are located at spaced locations with a defined air gap in the assembled state of the measuring head. The bars are arranged in the center of the measuring head in the area of the central axis of the housing parts (21, 2). A sample gas cuvette support (6) is provided in the air gap between the housing parts (21, 2) for positioning a sample gas cuvette holder (1). The sample gas cuvette support (6) is provided with a gas inlet and gas outlet (8, 81).

18 Claims, 2 Drawing Sheets

MEASURING HEAD FOR A DEVICE FOR MEASURING THE CONCENTRATION OF A PARAMAGNETIC GAS

FIELD OF THE INVENTION

The present invention pertains to a measuring head for a device for measuring the concentration of a paramagnetic gas in a gas sample, especially of oxygen in breathing gas.

BACKGROUND OF THE INVENTION

A prior-art device for measuring the concentration of a paramagnetic gas is described in DE 100 37 380 A1 and is characterized by a modulatable magnetic field source with an air gap, a modulation source for sending a modulation signal to the magnetic field source, a measuring element for generating a heat flux measurement signal, which is arranged at least partially within the air gap, is heated to a working temperature by a power source and by which a filter means connected to the measuring element for separating variations from the heat flux measured signal based on the modulation of the magnetic field, wherein the changing amplitude of the variations is an indicator of the percentage of the paramagnetic gas in the gas sample. The measurement of the oxygen concentration takes place in the air gap of an electrically modulatable magnet system, which air gap is equipped with a sample gas cuvette. On the one hand, it is difficult in the measuring systems used hitherto to prepare suitable coil cores with which the high magnetic flux densities in the air gap, which are necessary for a strong measured signal, can be generated with the sample gas cuvette in a reproducible manner. On the other hand, the narrow air gap must be prepared with geometric precision and very narrow tolerances for a reliable measurement. Finally, electric and magnetic interference fields shall be screened in order not to interfere with the measurement. Finally, mechanical protection of the measuring system is desirable. The current measuring arrangements are subject to these shortcomings.

SUMMARY OF THE INVENTION

The object of the present invention is to provide an improved measuring head with a precise air gap, with high magnetic field homogeneity and with screening against electromagnetic interference fields, wherein the measuring head additionally offers mechanical protection and comprises a small number of components.

According to the invention, a measuring head for a device for measuring the concentration of a paramagnetic gas in a gas sample as a function of the change in the thermal conductivity of the paramagnetic gas in a variable magnetic field is provided. The measuring head has first and second cylindrical housing parts made of a steel alloy for accommodating a magnet coil body, each extending concentrically around the central axis of each said housing part. Metallic cylindrical bars are used as magnet poles for the measuring head and are located at spaced locations with a defined air gap in the assembled state of the measuring head. These bars are arranged in the area of the central axis of the said housing parts. A sample gas cuvette support is provided in the air gap between the housing parts for positioning a sample gas cuvette holder. The sample gas cuvette support is provided with a gas inlet and a gas outlet.

An essential advantage of the measuring head in accordance with the invention is the compact design from the system components magnet system, sample gas cuvette support and housing, which can be manufactured in a relatively simple manner. The measuring head according to the present invention comprises a two-part cylindrical housing, whose longitudinal axial center has metallic, cylindrical bars used as magnet poles in the area of the central axis. The geometrically adapted first coil body is located in the first part of the cylindrical housing, while the second part of the housing accommodates a second coil body. The sample gas cuvette as well as the gas guide for the sample gas cuvette is either accommodated by the second part of the housing or is located alternatively in an additional module between the first and second parts of the housing.

The sample gas cuvette support may be formed by recesses for accommodating the sample gas cuvette holder in the second magnet coil body. At least one stationary sleeve may be provided for the connection to an external gas sampling system. The gas guide may extend via separate gas channels in the wall of the second magnet coil body in parallel to the central axis of the second housing part. The stationary sleeve for the connection to an external gas sampling system may be connected to the second magnet coil body.

An additional disk-shaped module equipped with the cuvette support and with the gas inlet and gas outlet may be inserted in an accurately fitting manner between the housing parts. The module may consist of a material not conducting the magnetic flux, especially a polysulfone (PSU) or material sold under the name POCAN®.

The housing parts may be made of machining steel, especially in one piece with the respective cylindrical bar associated with them.

The air gap between the cylindrical bars used as magnetic poles may be set and adjusted by means of a thread arranged on one of the bars.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
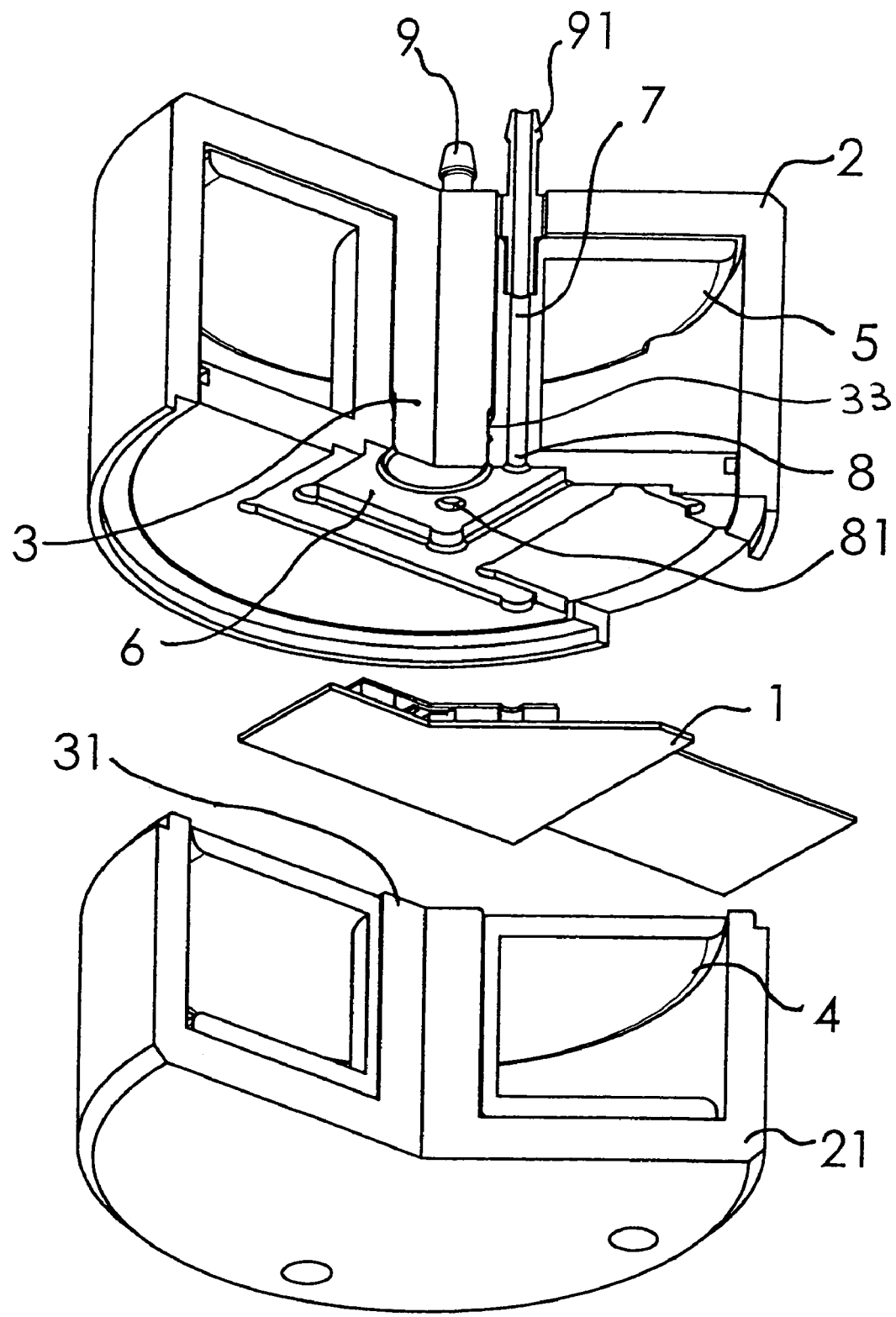
FIG. 1 is a sectional view through the system components of a first exemplary embodiment of the present invention.

Referring to the drawings in particular, the measuring head according to FIG. 1 comprises a two-part cylindrical housing with a first housing part 21, which is shown at the bottom of FIG. 1 and consists of a suitable steel alloy (machining steel) and can be machined with precision according to conventional manufacturing methods such as turning and milling. Cylindrical bars 31, 3 are used as magnet poles for the magnet system. Between these cylindrical bars 31, 3 a precise air gap is formed. Cylindrical bars 31, 3 are located in the longitudinal axial center of the central axis of the first and second housing parts 21, 2. The air gap may be set and adjusted by a bar 31 or 3 that can be rotated and axially moved, e.g., in a thread 33. The geometrically adapted first magnet coil body 4 is mounted in the first housing part 21 and forms the first part of the magnet system. The second part of the magnet system is formed by the second housing part 2, likewise made of a steel alloy. The second magnet coil body 5 with the integrated gas guide 7 as well as with a shaped sample gas cuvette support 6 is introduced into the second part of the magnet system.

The sample gas cuvette in the sample gas cuvette holder 1 is positioned in an accurately fitting manner and precisely in the sample gas cuvette support 6 between the housing parts 21, 2 and the cylindrical bars 31, 3 forming the magnet poles. The sample gas cuvette holder 1 is thus also protected mechanically. The assembled housing parts 2, 21 form the housing of the measuring head and are used to accommodate the magnet coil bodies 4, 5 and at the same time replace hitherto needed magnet coil cores, which are manufactured and mounted as separate components. Due to the shape selected, electromagnetic leakages to the environment are avoided and external electromagnetic disturbances are screened. In addition, a compact, robust and inexpensive design is guaranteed. The gas guide 7 for introducing and removing the gas sample is embodied by two gas channels in the wall of the second magnet coil body 5, which channels extend in parallel to the longitudinal axis of the cylindrical second housing part 2. The two gas channels open at the sample gas cuvette support 6 in the gas inlet and outlet 8, 81 of the sample gas cuvette holder 1. The connection to the external gas guide, e.g., to a gas sampling system of an anesthesia or respiration system, is established by two sleeves 9, 91 connected to the second housing part 2. The sleeves 9, 91 are used as tube connections for the external gas feed and removal.

Figure 2:
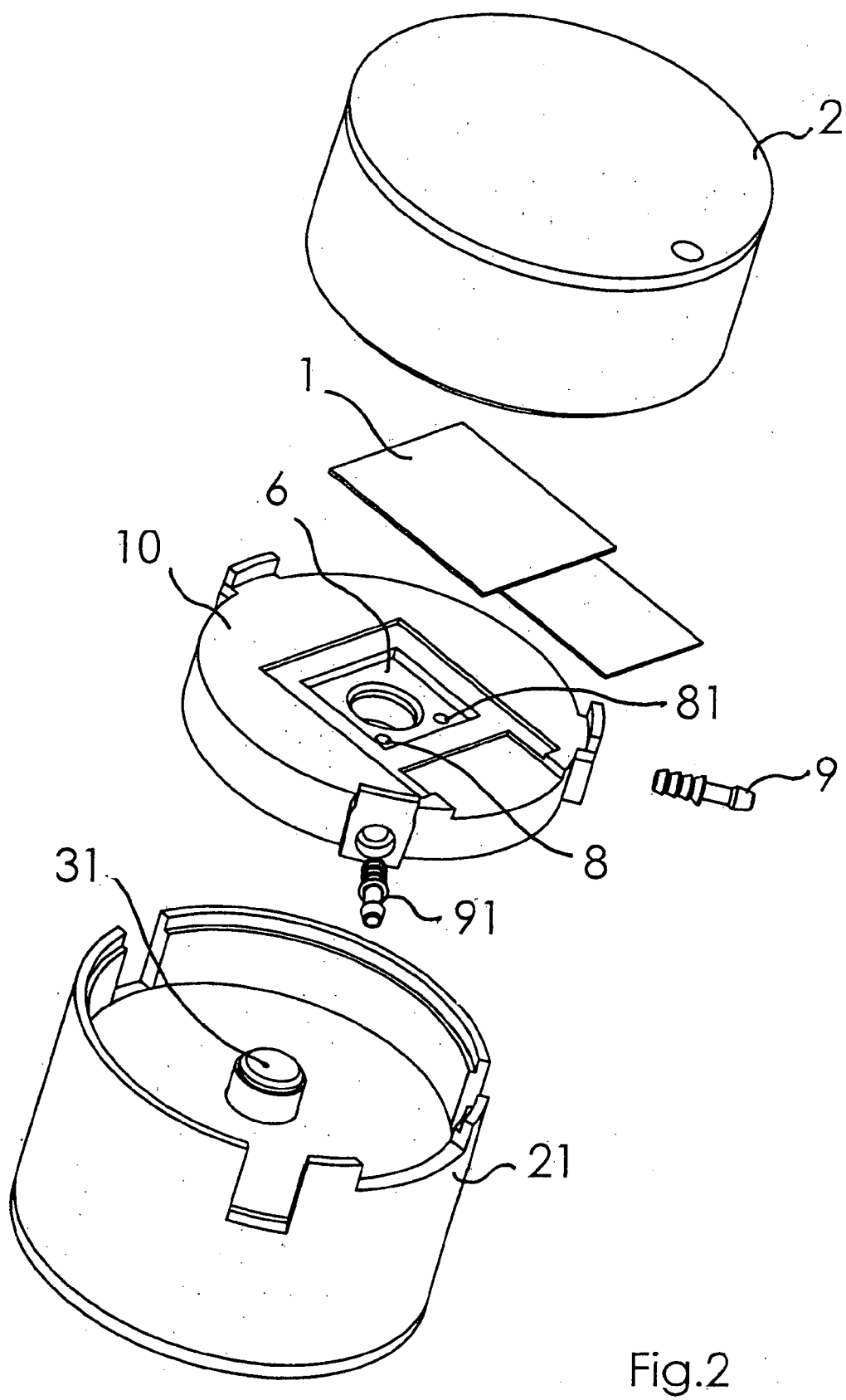
FIG. 2 is an exploded view of the system components of a second exemplary embodiment of the present invention.

FIG. 2 shows an alternative design of the measuring head, where identical parts are designated with the same reference numbers. The gas is guided by a module 10 that mechanically connects the two housing parts 2, 21 via webs and recesses and consists of a material not conducting the magnetic flux, specifically a plastic, especially a polysulfone or the material sold under the name POCAN® (polybutylene tetrephthalate (PBT)), which is integrated in the magnet system by fitting together the housing parts 2, 21. The module 10 thus couples the housing parts 2, 21 at a defined distance, establishes the gas guide, integrates the sample gas cuvette holder 1 including the sample gas cuvette, and protects same mechanically. The sample gas cuvette support 6 is located in the area of the central axis on the module 10. As in the first exemplary embodiment, gas is admitted into and removed from the sample gas cuvette via the gas inlet and outlet 8, 81. The connection to an external sampling system is established with the sleeves 9, 91 integrated within the module 10, as a consequence of which the gas sampling system is relieved of mechanical stress due to the module 10 and the coupling of the module with the rest of the magnet system. The interference of external mechanical effects on the sample gas cuvette holder 1 on the measurement is thus largely avoided. This equally applies to the exemplary embodiment according to FIG. 1 with the connection to an external gas sampling system via the sleeves 9, 91. Due to the gas flow being guided within the magnet system, the power loss of the magnet system guarantees the preheating of the gas sample to be measured, as a result of which rapid, nearly wattless regulation to the working temperature is possible in the interior of the sample gas cuvette.

For example, the lock-in method may be used as the signal processing method to measure the concentration of a paramagnetic gas in a gas sample and especially of oxygen in breathing gas based on the change in the thermal conductivity in changing magnetic fields, so that very weak measured signals are detected from the background noise and processed. Signal modulation is necessary for the application of such evaluation methods. A periodic change in the magnetic flux density, which is necessary to change the thermal conductivity of the paramagnetic gas to be measured, can be generated at the site of the sample gas cuvette by means of a sine control of the magnet system in the measuring head especially with the positive and negative half-waves. The change in the thermal conductivity caused per half-wave of the sine control of the magnet system is accompanied by a temperature change detected by a heated thermocouple arrangement. The temperature change of the gas to be measured takes place per half-wave of the sine control, i.e., with twice the frequency of the excitation frequency.

While specific embodiments of the invention have been shown and described in detail to illustrate the application of the principles of the invention, it will be understood that the invention may be embodied otherwise without departing from such principles.

What is claimed is:

1. A measuring head for a device for measuring the concentration of a paramagnetic gas in a gas sample as a function of the change in the thermal conductivity of the paramagnetic gas in a variable magnetic field, the measuring head comprising:
    a first cylindrical housing part made of a steel alloy for accommodating a magnet coil body, said first cylindrical housing part extending concentrically around a central axis thereof;
    a second cylindrical housing part made of a steel alloy for accommodating another magnet coil body, said second cylindrical housing part extending concentrically around a central axis of each housing part;
    a first metallic cylindrical bar arranged in the area of the central axis of said first housing part for use as a magnet pole for the measuring head;
    a second metallic cylindrical bar arranged in the area of the central axis of said second housing part for use as a magnet pole for the measuring head, said first metallic cylindrical bar and said second metallic cylindrical bar being located at spaced locations with a defined air gap in the assembled state of the measuring head;
    a sample gas cuvette support provided in the air gap between the housing parts for positioning a sample gas cuvette holder, said sample gas cuvette support being provided with a gas inlet and gas outlet, wherein the sample gas cuvette support is formed by recesses for accommodating the sample gas cuvette holder in the magnet coil body.

2. A measuring head in accordance with claim 1, further comprising: a stationary sleeve provided for the connection to an external gas sampling system.

3. A measuring head in accordance with claim 2, further comprising a gas guide extending via separate gas channels in the wall of the second magnet coil body in parallel to the central axis of the second housing part, and a stationary sleeve for connection of an external gas sampling system to the second magnet coil body.

4. A measuring head for a device for measuring the concentration of a paramagnetic gas in a gas sample as a function of the change in the thermal conductivity of the paramagnetic gas in a variable magnetic field, the measuring head comprising:

a first cylindrical housing part made of a steel alloy for accommodating a magnet coil body, said first cylindrical housing part extending concentrically around a central axis thereof;

a second cylindrical housing part made of a steel alloy for accommodating another magnet coil body, said second cylindrical housing part extending concentrically around a central axis of each housing part;

a first metallic cylindrical bar arranged in the area of the central axis of said first housing part for use as a magnet pole for the measuring head;

a second metallic cylindrical bar arranged in the area of the central axis of said second housing part for use as a magnet pole for the measuring head, said first metallic cylindrical bar and said second metallic cylindrical bar being located at spaced locations with a defined air gap in the assembled state of the measuring head;

a sample gas cuvette support provided in the air gap between the housing parts for positioning a sample gas cuvette holder, said sample gas cuvette support being provided with a gas inlet and gas outlet; and an additional disk-shaped module including said cuvette support and said gas inlet and said gas outlet, said additional disk-shaped module being inserted in an accurately fitting manner between said first housing part and said second housing part.

5. A measuring head in accordance with claim 1, wherein said first housing part and said second housing part are made of machining steel.

6. A measuring head in accordance with claim 5, wherein said first housing part is formed as one piece with said first cylindrical bar, and said second housing part is formed as one piece with said second cylindrical bar.

7. A measuring head in accordance with claim 4, wherein said module consists of a material not conducting the magnetic flux.

8. A measuring head in accordance with claim 7, wherein said module is a polysulfone (PSU) or polybutylene terephthalate (PBT).

9. A measuring head in accordance with claim 1, wherein the air gap between the cylindrical bars used as magnetic poles is set and adjusted by means of a thread arranged on one of the bars.

10. A paramagnetic gas concentration measuring head for measuring a change in the thermal conductivity of a paramagnetic gas in a variable magnetic field, the measuring head comprising:

a first magnet coil body;

a first housing part made of a steel alloy for accommodating said first magnet coil body;

a second magnet coil body;

a second cylindrical housing part made of a steel alloy for accommodating said second magnet coil body;

a first metallic bar arranged centrally in said first housing part for use as a magnet pole for the measuring head;

a second metallic bar arranged centrally in said second housing part for use as a magnet pole for the measuring head, said first metallic bar and said second metallic bar being located at spaced locations with a defined air gap in the assembled state of the measuring head;

a sample gas cuvette holder; and a sample gas cuvette support provided in the air gap between said first housing part and said second housing part of positioning said sample gas cuvette holder, said sample gas cuvette support being provided with a gas inlet and gas outlet, wherein the sample gas cuvette support is formed by recesses in the magnet coil body for accommodating said sample gas cuvette holder.

11. A measuring head in accordance with claim 10, further comprising: a stationary sleeve provided for the connection to an external gas sampling system.

12. A measuring head in accordance with claim 11, further comprising a gas guide extending via separate gas channels in the wall of the second magnet coil body in parallel to the central axis of the second housing part, and a stationary sleeve for connection of an external gas sampling system to the second magnet coil body.

13. A measuring head in accordance with claim 10, further comprising: an additional disk-shaped module including said cuvette support and said gas inlet and said gas outlet, said additional disk-shaped module being inserted in an accurately fitting manner between said first housing part and said second housing part.

14. A measuring head in accordance with claim 10, wherein said first housing part and said second housing part are made of machining steel.

15. A measuring head in accordance with claim 14, wherein said first housing part is formed as one piece with said first cylindrical bar and said second housing part is formed as one piece with said second cylindrical bar.

16. A measuring head in accordance with claim 13, wherein said module consists of a material not conducting the magnetic flux.

17. A measuring head in accordance with claim 16, wherein said module is a polysulfone (PSU) or polybutylene terephthalate (PBT).

18. A measuring head in accordance with claim 10, wherein the air gap between the cylindrical bars used as magnetic poles is set and adjusted by means of a thread arranged on one of the bars.

* * * * *